United States Patent
Barker

(10) Patent No.: US 8,364,284 B2
(45) Date of Patent: Jan. 29, 2013

(54) IMPLANTABLE ELECTRIC STIMULATION SYSTEM AND METHODS OF MAKING AND USING

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 721 days.

(21) Appl. No.: 12/210,451

(22) Filed: Sep. 15, 2008

(65) Prior Publication Data

US 2010/0070009 A1    Mar. 18, 2010

(51) Int. Cl.
*A61N 1/05* (2006.01)

(52) U.S. Cl. ........ 607/117; 607/115; 607/116; 607/119; 607/122; 607/123; 600/585; 604/43; 604/171

(58) Field of Classification Search .......... 607/115–116, 607/119, 122–123; 600/585; 604/43, 171
See application file for complete search history.

(56) References Cited

U.S. PATENT DOCUMENTS

| | | | |
|---|---|---|---|
| 5,156,151 A | 10/1992 | Imran | |
| 5,184,620 A | 2/1993 | Cudahy et al. | |
| 5,228,442 A | 7/1993 | Imran | |
| 5,239,999 A | 8/1993 | Imran | |
| 5,279,299 A | 1/1994 | Imran | |
| 5,404,638 A | 4/1995 | Imran | |
| 5,406,946 A | 4/1995 | Imran | |
| 5,450,758 A | 9/1995 | Smoll | |
| 5,722,401 A | 3/1998 | Pietroski et al. | |
| 5,935,159 A | 8/1999 | Cross, Jr. et al. | |
| 6,181,969 B1 | 1/2001 | Gord | |
| 6,217,525 B1 | 4/2001 | Medema et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,650,945 B2 * | 11/2003 | Helland et al. ........ 607/122 |
| 6,741,892 B1 | 5/2004 | Meadows et al. | |
| 7,096,063 B2 | 8/2006 | Wanasek et al. | |
| 7,103,398 B2 | 9/2006 | Sieburg | |

(Continued)

FOREIGN PATENT DOCUMENTS

| | | |
|---|---|---|
| EP | 499491 | 8/1992 |
| EP | 771547 | 5/1997 |

(Continued)

OTHER PUBLICATIONS

U.S. Appl. No. 11/238,240, filed Sep. 29, 2005.

*Primary Examiner* — Carl H Layno
*Assistant Examiner* — Deborah Malamud
(74) *Attorney, Agent, or Firm* — Frommer Lawrence & Haug; Patrick R. Turner

(57) ABSTRACT

A lead assembly includes a lead with a distal end and a proximal end. The lead includes a plurality of electrodes disposed at the distal end and a plurality of terminals disposed at the proximal end. The lead also defines at least one central lumen and a plurality of outer lumens. The central and outer lumens extend from the proximal end to the distal end such that the plurality of outer lumens extend laterally from the at least one central lumen. The lead further includes a plurality of conductive wires. Each conductive wire couples at least one of the plurality of electrodes electrically to at least one of the plurality of terminals. At least two conductive wires are disposed in each of the plurality of outer lumens.

20 Claims, 10 Drawing Sheets

U.S. PATENT DOCUMENTS

| | | |
|---|---|---|
| 7,136,702 B2 | 11/2006 | Wanasek |
| 7,149,583 B1 | 12/2006 | Litvak |
| 7,199,110 B2 | 4/2007 | Borgens et al. |
| 7,244,150 B1 | 7/2007 | Brase et al. |
| 7,277,760 B1 | 10/2007 | Litvak et al. |
| 7,286,878 B2 | 10/2007 | Stypulkowski |
| 7,317,945 B2 | 1/2008 | Litvak et al. |
| 2002/0183824 A1 | 12/2002 | Borgersen et al. |
| 2003/0077943 A1 | 4/2003 | Osypka |
| 2003/0114905 A1 | 6/2003 | Kuzma |
| 2004/0059392 A1 | 3/2004 | Parramon et al. |
| 2004/0230243 A1 | 11/2004 | Haefner et al. |
| 2004/0260355 A1 | 12/2004 | Holleman et al. |
| 2004/0260373 A1 | 12/2004 | Ries et al. |
| 2005/0004627 A1 | 1/2005 | Gibson et al. |
| 2005/0015133 A1 | 1/2005 | Ibrahim et al. |
| 2005/0165465 A1 | 7/2005 | Pianca et al. |
| 2005/0261748 A1 | 11/2005 | van Dijk |
| 2006/0116738 A1 | 6/2006 | Wolf et al. |
| 2006/0129210 A1 | 6/2006 | Cantin et al. |
| 2006/0287690 A1 | 12/2006 | Bouchataoui et al. |
| 2007/0123963 A1 | 5/2007 | Krulevitch |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0203537 A1 | 8/2007 | Goetz et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0219595 A1 | 9/2007 | He |
| 2007/0239243 A1 | 10/2007 | Moffitt et al. |
| 2008/0071320 A1 | 3/2008 | Brase |
| 2008/0140152 A1 | 6/2008 | Imran et al. |
| 2008/0177343 A1 | 7/2008 | Dal Molin et al. |

FOREIGN PATENT DOCUMENTS

| | | |
|---|---|---|
| EP | 1790380 | 5/2007 |
| WO | WO-03003791 | 1/2003 |
| WO | 03035173 A1 | 5/2003 |
| WO | WO-03035168 | 5/2003 |
| WO | WO-2004023235 | 3/2004 |
| WO | WO-2007097858 | 8/2007 |
| WO | WO-2007097859 | 8/2007 |
| WO | WO-2007097861 | 8/2007 |
| WO | WO-2007097873 A1 | 8/2007 |
| WO | WO-2007100427 | 9/2007 |

* cited by examiner

Fig. 10A       Fig. 10B       Fig. 10C

IMPLANTABLE ELECTRIC STIMULATION SYSTEM AND METHODS OF MAKING AND USING

TECHNICAL FIELD

The present invention is directed to the area of implantable electrical stimulation systems and methods of making and using the systems. The present invention is also directed to implantable electrical stimulation systems that include a lead utilizing strategies to increase the number of electrodes preferably without a corresponding increase in the lateral circumference of the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead assembly includes a lead with a distal end and a proximal end. The lead includes a plurality of electrodes disposed at the distal end and a plurality of terminals disposed at the proximal end. The lead also defines at least one central lumen and a plurality of outer lumens. The central and outer lumens extend from the proximal end to the distal end such that the plurality of outer lumens extend laterally from the at least one central lumen. The lead further includes a plurality of conductive wires. Each conductive wire couples at least one of the plurality of electrodes electrically to at least one of the plurality of terminals. At least two conductive wires are disposed in each of the plurality of outer lumens.

In another embodiment, an electrical stimulating system includes a lead, a control module, and a connector. The lead includes a plurality of electrodes disposed at the distal end and a plurality of terminals disposed at the proximal end. The lead also defines at least one central lumen and a plurality of outer lumens. The central and outer lumens extend from the proximal end to the distal end such that the plurality of outer lumens extend laterally from the at least one central lumen. The lead further includes a plurality of conductive wires. Each conductive wire couples at least one of the plurality of electrodes electrically to at least one of the plurality of terminals. At least two conductive wires are disposed in each of the plurality of outer lumens. The control module is configured and arranged to electrically couple to the lead. The control module includes a housing and an electronic subassembly disposed in the housing. The connector is configured and arranged for receiving the lead. The connector includes a connector housing and a plurality of connector contacts disposed in the connector housing. The connector housing defines at least one port for receiving the proximal end of the lead. The connector contacts are configured and arranged to couple to at least one terminal disposed at the proximal end of the lead.

In yet another embodiment, a method for making a lead includes placing a substantially tubular-shaped lead body, with a proximal end and a distal end, into a mold with mold cavities between spaced-apart cylindrical pockets. The lead body includes a plurality of conductive wires in each of a plurality of outer lumens. The outer lumens extend out of both the proximal end and the distal end of the lead body. A plurality of terminals are disposed over the portion of the outer lumens extending out of the proximal end of the lead body so that the each terminal aligns with a different cylindrical pocket. Each terminal is electrically coupled to a different conductive wire. A plurality of electrodes are disposed over the portion of the outer lumens extending out of the distal end of the lead body so that the each electrode aligns with a different cylindrical pocket. Each electrode is electrically coupling to a different conductive wire. Resin is injected into the mold cavities between the spaced-apart cylindrical pockets.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10A is a schematic side view of one embodiment of a portion of a proximal end of a lead of an electrical stimulation system, according to the invention;

FIG. 10B is a schematic side view of one embodiment of a portion of an end plug configured and arranged for disposal in a proximal end of a lead of an electrical stimulation system, according to the invention;

FIG. 10C is a schematic side view of one embodiment of an end plug disposed in a proximal end of a lead of an electrical stimulation system, according to the invention;

DETAILED DESCRIPTION

The present invention is directed to the area of implantable electrical stimulation systems and methods of making and using the systems. The present invention is also directed to implantable electrical stimulation systems that include a lead with an increased number of electrodes without a corresponding increase in the lateral circumference of the lead, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
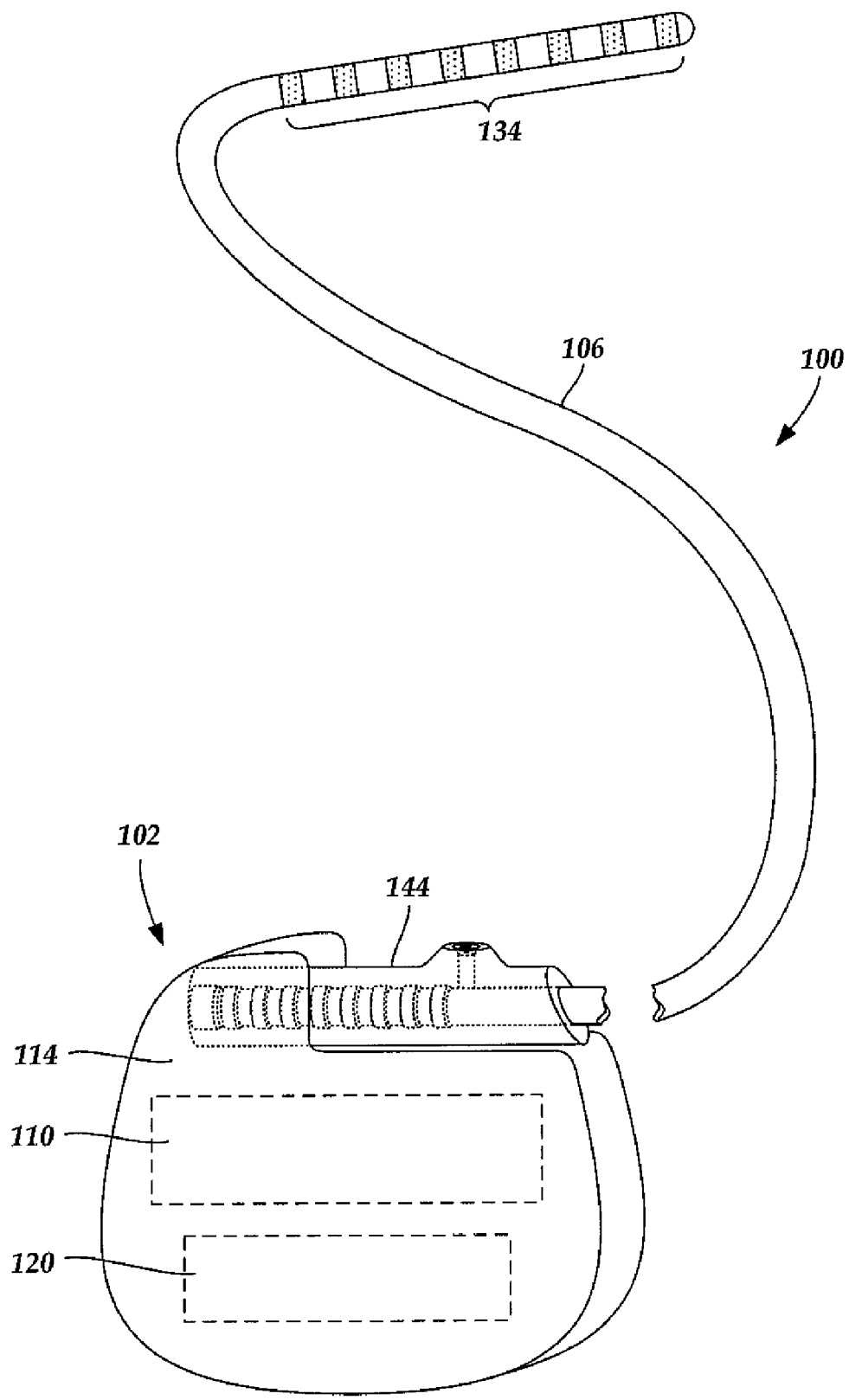
FIG. 1 is a schematic view of one embodiment of an electrical stimulation system, according to the invention.

FIG. 1 illustrates schematically one embodiment of an electrical stimulation system 100. The electrical stimulation system 100 includes a control module (e.g., a stimulator or pulse generator) 102 and at least one percutaneous lead ("lead") 106 that includes an array of electrodes 134 at a distal end. The control module 102 typically includes an electronic subassembly 10 and an optional power source 120 disposed in a sealed housing 114. The control module 102 typically includes a connector 144 (see also FIG. 2A, and 222 and 250 of FIG. 2B) into which the proximal end of the one or more leads 106 can be plugged to make an electrical connection via connector contacts on the control module 102 and terminals (e.g., 210 in FIG. 2A and 236 of FIG. 2B) on each of the one or more leads 106. It will be understood that the electrical stimulation system can include more, fewer, or different components and can have a variety of different configurations including those configurations disclosed in the electrical stimulation system references cited herein. A lead may be isodiametric along the length of the lead. In addition, one or more lead extensions 212 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the one or more leads 106 are typically disposed in, or separated by, a non-conductive, biocompatible material including, for example, silicone, polyurethane, polyetheretherketone ("PEEK"), epoxy, and the like or combinations thereof. The one or more leads 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more leads 106.

Terminals (e.g., 210 in FIG. 2A and 236 of FIG. 2B) are typically disposed at the proximal end of the one or more leads 106 for connection to corresponding connector contacts (e.g., 214 in FIG. 2A and 240 of FIG. 2B) in connectors (e.g., 144 in FIGS. 1-2A and 222 and 250 of FIG. 2B) disposed on, for example, the control module 102 (or to other devices, such as connector contacts on a lead extension, an operating room cable, or an adaptor). Conductive wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In some embodiments, each terminal (e.g., 210 in FIG. 2A and 236 of FIG. 2B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
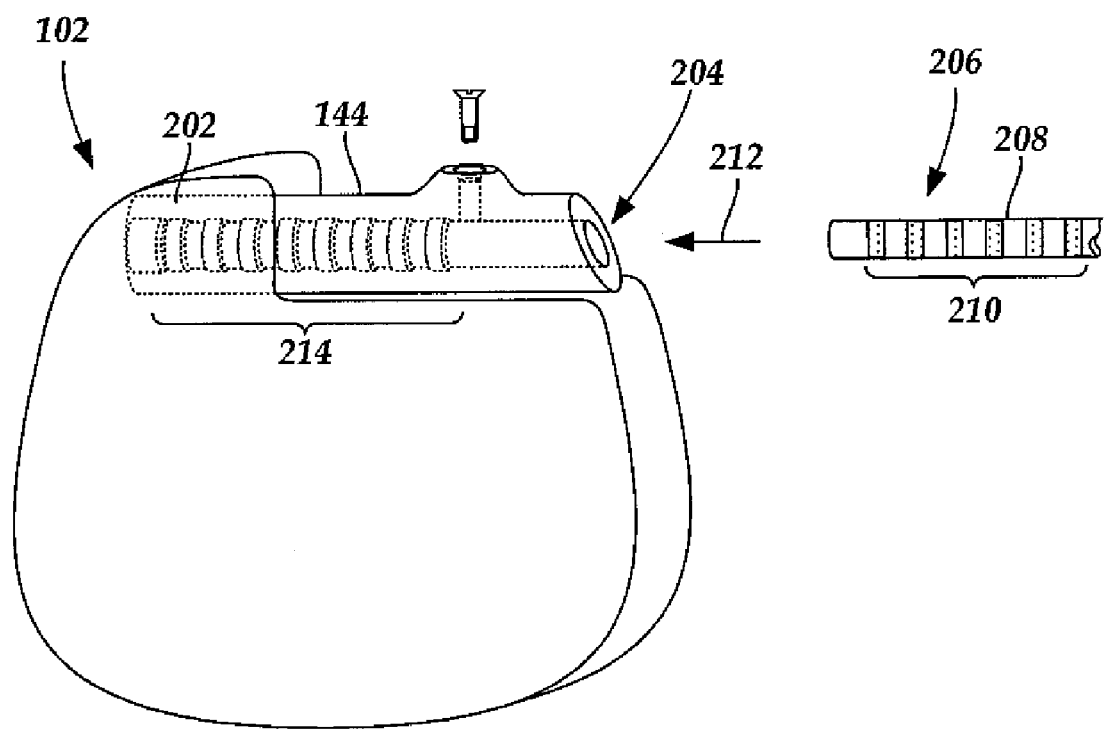
FIG. 2A is a schematic view of one embodiment of a proximal portion of a lead and a control module of an electrical stimulation system, according to the invention.

In at least some embodiments, leads are coupled with connectors disposed as part of a control module. In at least some embodiments, leads are coupled with connectors disposed on lead extensions. In other embodiments, leads are coupled with connectors disposed on other devices, such as an operating room cable or an adaptor. In at least some embodiments, fastening assemblies can be used to secure a coupling of a lead with a connector. In FIG. 2A, the connector 144 is shown disposed on the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of connector contacts 214 for each port 204. When the lead 208 is inserted into the port 204, the connector contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. No. 7,244,150 and U.S. patent application Ser. No. 11/532,844, which are incorporated by reference.

Figure 2B:
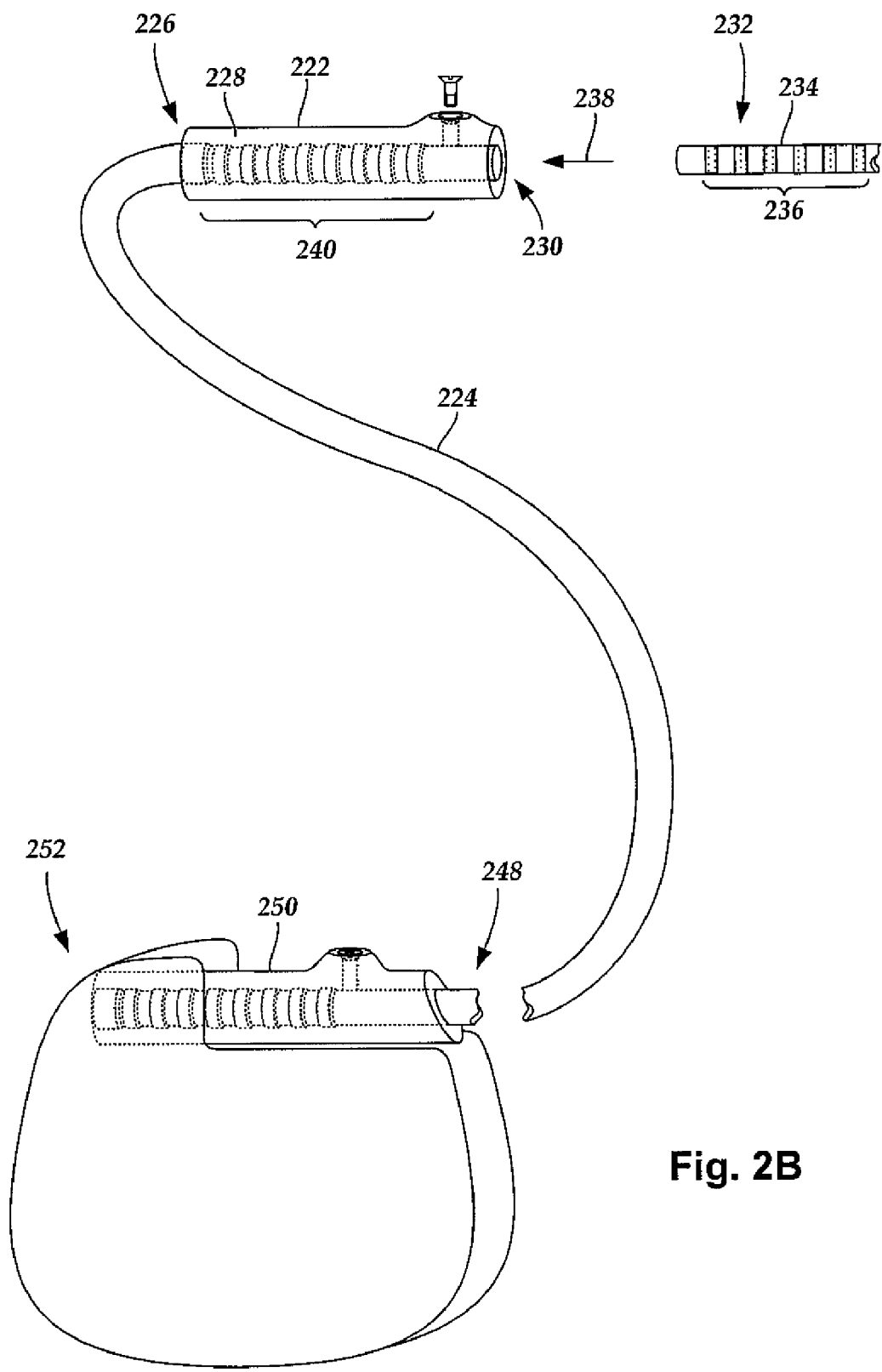
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of connector contacts 240. When the lead 234 is inserted into the port 230, the connector contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged to a proximal end of a lead. The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. For example, in FIG. 2B the proximal end 248 of the lead extension 224 is inserted into a connector 250 disposed in a control module 252. Note that, when a lead includes two or more proximal ends, each proximal end can be inserted into one of a plurality of ports defined in a connector, with each port including a plurality of connector contacts.

Sometimes a patient may be experiencing pain that extends to an area greater in length than the length of an array of electrodes (e.g., 134 of FIG. 1) disposed on the distal end of a particular lead. For example, a patient may experience pain in an area spanning multiple vertebral bodies. One way to increase stimulation coverage is to provide a lead with a greater length and either increase the amount of space between adjacent electrodes, or increase the size of one or more of the electrodes. However, when the amount of space between adjacent electrodes is increased or the size of one or more of the electrodes in increased, linear electrode density may decrease to a sub-therapeutic level.

Another way to increase stimulation coverage is to provide a lead with a greater length and increase the number of electrodes on the lead. A lead with additional electrodes may include additional conductive wires. When an increased number of conductive wires are utilized, existing control modules may not be compatible with the lead. One option is to redesign a control module to accommodate the additional electrodes. A redesigned control module may include a larger-sized connector, as well as a corresponding increase in the size or complexity of associated electronics. A larger-sized connector and additional electronics disposed in a control module may increase the size of the control module and accordingly make the control module difficult to manufacture or less convenient to implant in a patient. Additionally, an increased number of conductive wires extending the length of a lead can increase the lateral circumference of a lead, which may decrease the maneuverability or implantability of the lead and also potentially reducing the number of potential implantation locations.

In at least some embodiments, more stimulation coverage can be provided without increasing the size or the complexity of a corresponding control module. In at least some embodiments, a proximal end of a lead with an increased number of conductive wires is inserted into a connector disposed on a lead splitter with multiple proximal tails. Each proximal tail is configured and arranged to electrically couple electrodes disposed on the lead to at least one connector contact disposed in a connector disposed on a control module. Thus, in at least some embodiments, each proximal tail of the lead splitter can plug into a separate connector on the control module.

Figure 3:
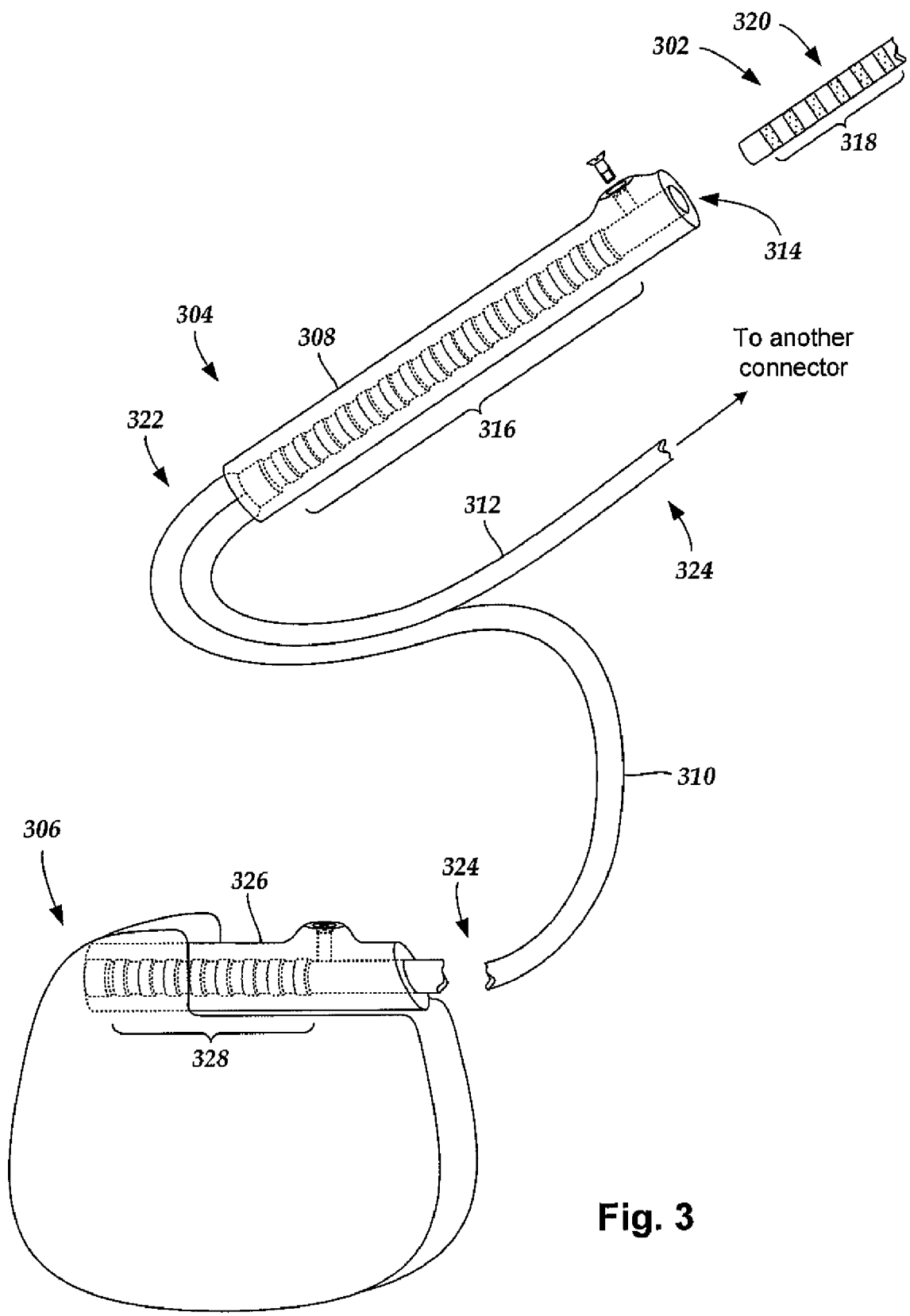
FIG. 3 is a schematic view of another embodiment of a proximal portion of a lead and a lead splitter of an electrical stimulation system, according to the invention.

FIG. 3 is a schematic view of another embodiment of a proximal end of a lead 302 configured and arranged for insertion into a lead splitter 304 that is electrically coupled to a control module 306. The lead splitter 304 includes a connector 308 and proximal tails 310 and 312. The connector 308 defines a port 314 that includes a plurality of conductor contacts 316 disposed in the port 314. The lead 302 includes a plurality of terminals 318 on a proximal end 320 that are configured and arranged for insertion into the port 314 for electrically coupling with the plurality of conductor contacts 316. The proximal tails 310 and 312 each include a distal end 322 and a proximal end 324. Each of the distal ends 322 is coupled to at least one of the plurality of conductor contacts 316. Each of the proximal ends 324 is configured and arranged to couple to other connectors, such as the connector 326 disposed in the control module 306, via conductive wires (not shown). For example, conductive wires disposed in the proximal tail 310 extend the longitudinal length of the proximal tail 310 and electrically couple one or more of the plurality of connector contacts 316 to the connector contacts 328 disposed in the connector 326.

In at least some embodiments, approximately half of the connector contacts 316 electrically couple with conductive wires extending the longitudinal length of the proximal tail 310 and half of the connector contacts 316 electrically couple with conductive wires extending the longitudinal length of the proximal tail 312. In one embodiment, the lead 302 includes sixteen terminals 318 corresponding with sixteen electrodes (not shown). The connector 308 includes sixteen conductor contacts 316 configured and arranged to electrically couple with the sixteen terminals 318 of the lead 302. Eight conductive wires are disposed in the proximal tail 310 and electrically couple with eight of the sixteen conductor contacts 316, while eight other conductive wires are disposed in the proximal tail 312 and electrically couple with the remaining eight of the sixteen conductor contacts 316.

The number of proximal tails 310 and 312 disposed on the lead splitter 304 may vary. For example, there can be two, four, six, eight, ten, twelve, fourteen, sixteen, or more proximal tails 310 and 312. As will be recognized, other numbers of proximal tails 310 and 312 may also be used. Accordingly, in some embodiments, each proximal tail 310 and 312 electrically couples a portion of the connector contacts 316 to two or more control modules. Thus, two or more control modules may be used to provide electric signals to a plurality of electrodes disposed on the lead 302.

In FIG. 3 and in subsequent figures, eight electrodes are used as an example of the number of electrodes disposed on a distal end of a lead. Thus, sixteen electrodes are used as an example of a doubling of the number of electrodes disposed on a distal end of a lead. Additionally, sixteen terminals, sixteen connector contacts, and sixteen conductive wires are used as examples of a one-to-one relationship between the number of electrodes and the number of corresponding terminals, connector contacts, and conductive wires disposed on leads and corresponding connectors when the number of electrodes disposed on a lead is doubled. The numbers eight and sixteen and the one-to-one relationship are used merely for the purposes of illustration. Other numbers of electrodes may be disposed on a lead and other non-one-to-one relationships may likewise be used in at least some embodiments. For example, in alternate embodiments, a lead may have eight electrodes that electrically couple with four terminals. The six terminals may, in turn, electrically couple with eight connector contacts.

Figure 4:
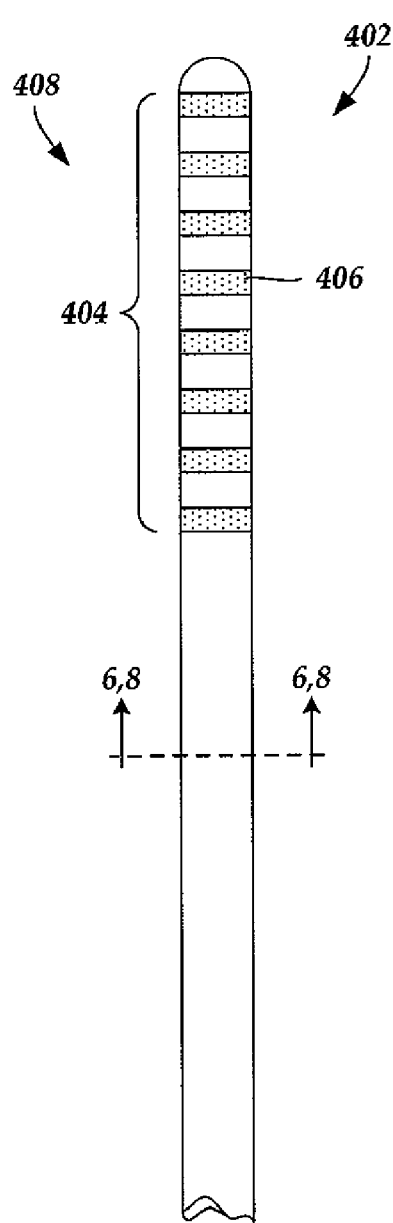
FIG. 4 is a schematic side view of a portion of a distal end of a currently-known lead of an electrical stimulation system, according to the invention.

In at least some embodiments, the number of electrodes disposed on a lead can be increased up to a factor of two from a conventional number of electrodes without increasing the lateral circumference of the lead. Thus, in at least some embodiments, additional electrodes can be added to conventional leads, while still allowing the leads with additional electrodes to be compatible with conventional control modules. FIG. 4 is a schematic side view of one embodiment of a portion of a distal end of an exemplary conventional lead 402. The exemplary conventional lead 402 includes a plurality of electrodes 404, such as electrode 406, disposed on a distal end 408 of the exemplary conventional lead 402. Additional features of the exemplary conventional lead 402 are described below, with respect to FIGS. 6 and 8, for comparison with at least some embodiments.

Figure 5:
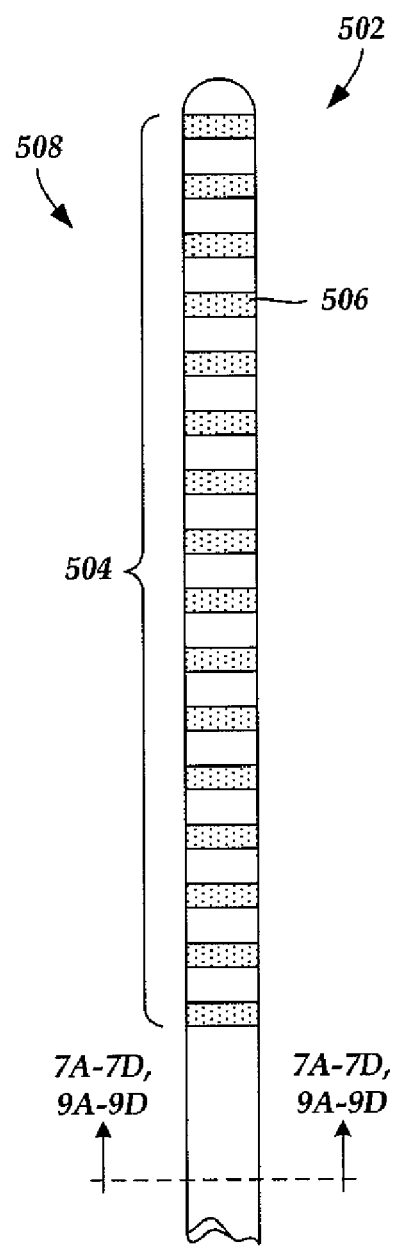
FIG. 5 is a schematic side view of another embodiment of a portion of a distal end of a lead of an electrical stimulation system, according to the invention.

FIG. 5 is a schematic side view of one embodiment of a portion of a distal end of a lead 502 with a lateral circumference that is equal to the lateral circumference of the exemplary conventional lead 402, but that includes twice the number of electrodes from the lead 402. The lead 502 includes a plurality of electrodes 504, such as electrode 506, disposed on a distal end 508 of the lead 502. The plurality of electrodes 504 is greater than the plurality of electrodes 404 in FIG. 4 without a corresponding increase in the lateral circumference of the lead 502. In a preferred embodiment, the number of electrodes disposed on the lead 502 is twice the number of electrodes disposed on the lead 402. For example, in FIG. 4, eight electrodes are shown on the lead 402, while in FIG. 5 sixteen electrodes are shown on the lead 502. In one embodiment, the leads 402 and 502 are each isodiametric and have a lateral diameter of 0.053 inches (0.135 cm).

Figure 6:
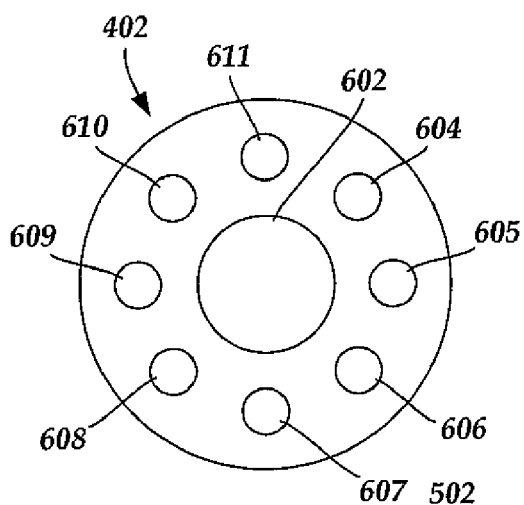
FIG. 6 is a schematic transverse cross-sectional view of one embodiment of the lead shown in FIG. 4, according to the invention.

Conductive wires may be used to electrically couple electrodes on a distal end of a lead to terminals on a proximal end of a lead. As discussed above, with reference to FIG. 1, conductive wires may be embedded in the non-conductive material of the lead or can be disposed in one or more lumens extending along the lead. In some embodiments, each individual conductive wire is disposed in an individual lumen. FIG. 6 is a schematic transverse cross-sectional view of the distal end of the exemplary conventional lead 402 shown in FIG. 4. In FIG. 6, the lead 402 includes a center lumen 602 and a plurality of outer lumens 604-611. Each outer lumen 604-611 is configured and arranged for an individual conductive wire to extend along the length of each individual outer lumen 604-611. In FIG. 6, eight circular-shaped outer lumens 604-611 are shown. Thus, in the conventional lead 402 shown in FIG. 4, eight connector wires can be disposed in the outer lumens 604-611 and electrically coupled to eight electrodes.

FIGS. 7A-7D show four different embodiments of transverse cross-sectional views of the lead 502 that are each configured and arranged to receive up to twice as many conductive wires as the conventional lead 402 shown in FIGS. 4 and 6 without a corresponding increase in the lateral circumference of the lead 502. Accordingly, in at least some embodiments, up to twice the number of conductive wires may be disposed in the lead 502 from the exemplary conventional lead 402 and electrically couple with up to twice the number of electrodes disposed on the distal end of the lead 502 from the exemplary conventional lead 502.

Figure 7A:
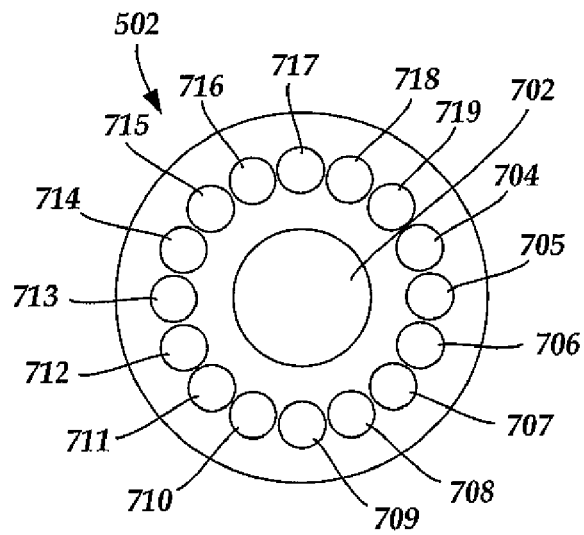
FIG. 7A is a schematic transverse cross-sectional view of one embodiment of the lead shown in FIG. 5, according to the invention.

In some embodiments, a single conductive wire extends through each outer lumen. FIG. 7A is a schematic transverse cross-sectional view of one embodiment of the distal end of the lead 502. In FIG. 7A, the lead 502 includes a center lumen 702 and a plurality of outer lumens 704-719. Each outer lumen 704-719 is configured and arranged for an individual conductive wire to extend along the length of each individual outer lumen 704-719. In FIG. 7A, sixteen circular-shaped outer lumens 704-719 are shown. Thus, in some embodiments, sixteen connector wires can be disposed in the outer lumens 704-719 and electrically coupled to sixteen electrodes.

Figure 7B:
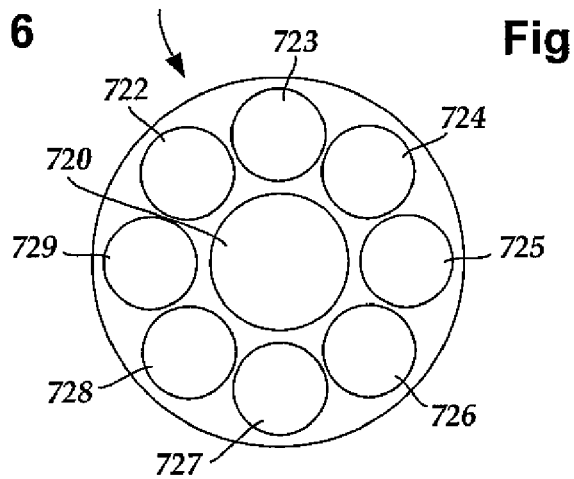
FIG. 7B is a schematic transverse cross-sectional view of a second embodiment of the lead shown in FIG. 5, according to the invention.

In other embodiments, two or more conductive wires may extend through each outer lumen. FIG. 7B is a schematic transverse cross-sectional view of a second embodiment of the distal end of the lead 502. In FIG. 7B, the lead 502 includes a center lumen 720 and a plurality of outer lumens 722-729. Each outer lumen 722-729 is configured and arranged for multiple conductive wires to extend along the length of each individual outer lumen 722-729. In FIG. 7B, eight circular-shaped outer lumens 722-729 are shown, with each outer lumen 722-729 configured and arranged for two conductive wires to extend within each outer lumen 722-729. Thus, in some embodiments, sixteen connector wires can be disposed in the outer lumens 722-729 and electrically coupled to sixteen electrodes.

Figure 7C:
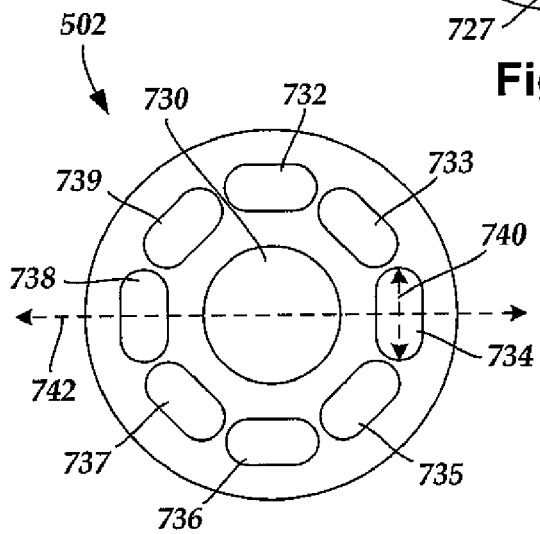
FIG. 7C is a schematic transverse cross-sectional view of a third embodiment of the lead shown in FIG. 5, according to the invention.

FIG. 7C is a schematic transverse cross-sectional view of a third embodiment of the distal end of the lead 502. In FIG. 7C, the lead 502 includes a center lumen 730 and a plurality of outer lumens 732-739. Each outer lumen 732-739 is configured and arranged for multiple conductive wires to extend along the length of each individual outer lumen 732-739. In FIG. 7C, eight oval-shaped outer lumens 732-739 are shown, with each outer lumen 732-739 configured and arranged for two conductive wires to extend within each outer lumen 732-739. Thus, in some embodiments, sixteen connector wires can be disposed in the outer lumens 732-739 and electrically coupled to sixteen electrodes. In FIG. 7C, the outer lumens 732-739 each include a major axis, such as the major axis 740, of the outer lumen 734. In FIG. 7C, the outer lumens 732-739 are oriented such that the major axis of each of the outer lumens 732-739 is approximately perpendicular to a diameter of the lead 502 which passed through a center of each of the outer lumens 732-739. For example, in FIG. 7C, the major axis 740 of the outer lumen 734 is approximately perpendicular to the diameter 742 extending through the center of the outer lumen 734.

Figure 7D:
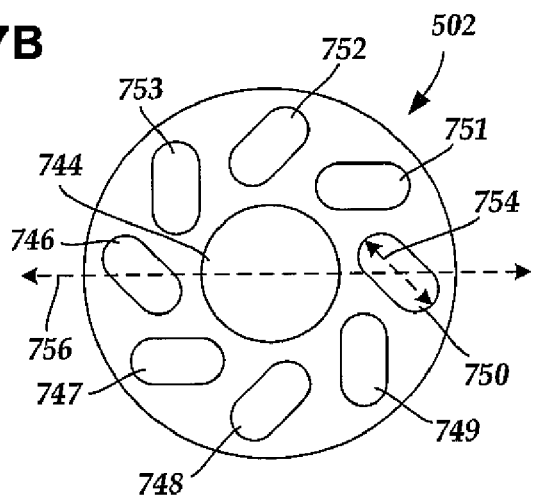
FIG. 7D is a schematic transverse cross-sectional view of a fourth embodiment of the lead shown in FIG. 5, according to the invention.

FIG. 7D is a schematic transverse cross-sectional view of a fourth embodiment of the distal end of the lead 502. In FIG. 7D, the lead 502 includes a center lumen 744 and a plurality of outer lumens 746-753. Each outer lumen 746-753 is configured and arranged for multiple conductive wires to extend along the length of each individual outer lumen 746-753. In FIG. 7D, eight oval-shaped outer lumens 746-753 are shown, with each outer lumen 746-753 configured and arranged for two conductive wires to extend within each outer lumen 746-753. Thus, in some embodiments, sixteen connector wires can be disposed in the outer lumens 746-753 and electrically coupled to sixteen electrodes. In FIG. 7D the outer lumens 746-753 each include a major axis, such as the major axis 754 of the outer lumen 750.

In FIG. 7D, the outer lumens 746-753 are oriented such that the major axis of each of the outer lumens 746-753 is disposed at a non-perpendicular angle with respect to a diameter of the lead 502 which passed through a center of each of the outer lumens 746-753. For example, in FIG. 7D, the major axis 754 of the outer lumen 750 is disposed at a non-perpendicular angle with respect to the diameter 756 extending through the center of the outer lumen 750. In at least some embodiments, each of the outer lumens 746-753 are disposed at an angle in the range of 15 to 75 degrees or 30 to 60 degrees, for example, at approximately a 45° angle, with respect to a diameter passing through a center of each of the outer lumens 746-753.

In alternate embodiments, outer lumens can be configured and arranged to accommodate additional conductive wires. Accordingly, the number of multiple conductive wires that can be disposed in an outer lumen may vary. For example, there can be one, two, three, four, five, six, seven, eight, nine, ten, twelve, fourteen, sixteen, or more conductive wires disposed in an outer lumen. As will be recognized, other numbers of conductive wires may also be disposed in an outer lumen.

Figure 8:
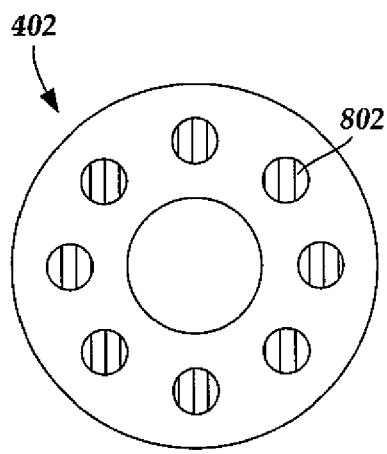
FIG. 8 is a schematic transverse cross-sectional view of one embodiment of a lead with a conductive wire disposed in each outer lumen of the lead shown in FIG. 4, according to the invention.
Figure 9A:
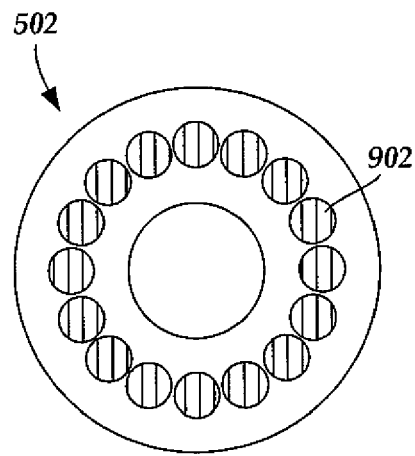
FIG. 9A is a schematic transverse cross-sectional view of one embodiment of a lead with a conductive wire disposed in each outer lumen of the lead shown in FIG. 5, according to the invention.

FIG. 8 is a schematic transverse cross-sectional view of one embodiment of a conductive wire disposed in each outer lumen of the exemplary conventional lead 402. In FIG. 8, an individual conductive wire, such conductive wire 802, is disposed in each of the outer lumens (604-611 in FIG. 6). FIG. 9A is a schematic transverse cross-sectional view of one embodiment of a conductive wire disposed in each outer lumen of the lead 502. In FIG. 9A, an individual conductive wire, such as the conductive wire 902, is disposed in each of the outer lumens (704-719 in FIG. 7A).

Figure 9B:
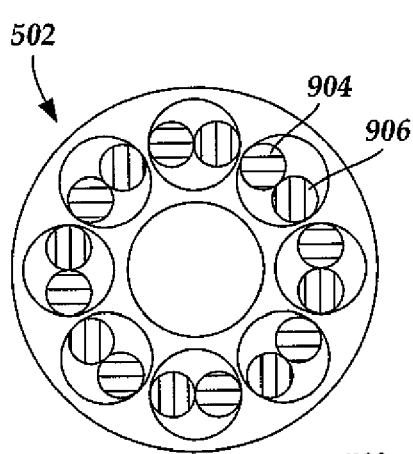
FIG. 9B is a schematic transverse cross-sectional view of one embodiment of a lead with multiple conductive wires disposed in each outer lumen of the lead shown in FIG. 5, according to the invention.

FIG. 9B is a schematic transverse cross-sectional view of one embodiment of multiple conductive wires disposed in each outer lumen of the lead 502. In FIG. 9B, two conductive wires, such as conductive wires 904 and 906, are shown disposed in each of the outer lumens (722-729 in FIG. 7B). In at least some embodiments, when multiple conductive wires are disposed in an individual outer lumen of a lead, an insulated coating disposed over each of the conductive wires is visually distinct from the insulated coating disposed over other conductive wires disposed in the same outer lumen to facilitate assembly or repair of a lead. For example, multiple conductive wires disposed in an individual outer lumen may include insulated coatings of different colors. In FIG. 9B and in subsequent figures, different cross-hatching is used for each conductive wire disposed in an outer lumen to signify that each conductive wire includes an insulated coating that is visually distinct from other conductive wires.

Figure 9C:
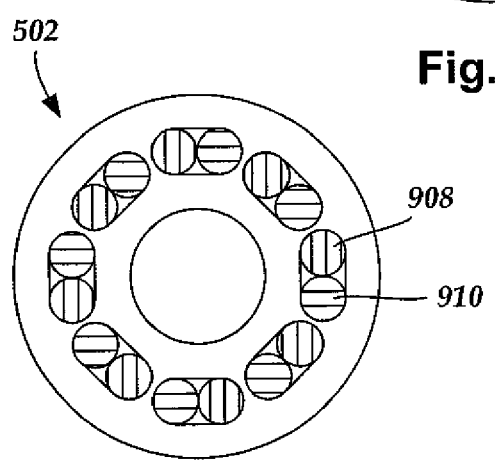
FIG. 9C is a schematic transverse cross-sectional view of a second embodiment of a lead with multiple conductive wires disposed in each outer lumen of the lead shown in FIG. 5, according to the invention.
Figure 9D:
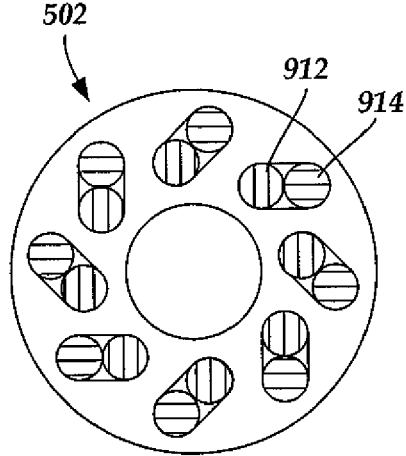
FIG. 9D is a schematic transverse cross-sectional view of a third embodiment of a lead with multiple conductive wires disposed in each outer lumen of the lead shown in FIG. 5, according to the invention.

FIG. 9C is a schematic transverse cross-sectional view of one embodiment of multiple conductive wires disposed in each outer lumen of the lead 502. In FIG. 9C, two conductive wires, such as conductive wires 908 and 910, are shown disposed in each of the outer lumens (732-739 in FIG. 7C). FIG. 9D is a schematic transverse cross-sectional view of one embodiment of multiple conductive wires disposed in each outer lumen of the lead 502. In FIG. 9D, two conductive wires, such as conductive wires 912 and 914, are shown disposed in each of the outer lumens (746-753 in FIG. 7D).

In some embodiments, an end plug can be disposed in a central lumen to stiffen a proximal end of a lead to facilitate insertion of the proximal end of the lead into a connector. FIG. 10A is a schematic side view of one embodiment of a portion of a proximal end of the lead 502. The proximal end 1004 of the lead 502 includes a plurality of terminals 1006, such as the terminal 1008, and a central lumen 1010. Note that, in FIG. 10A and in subsequent figures, only a subset of the terminals 1006 are shown for clarity of illustration. FIG. 10B is a schematic side view of one embodiment of a portion of an end plug 1012. The end plug 1012 includes an end cap 1014 and a rod 1016 mounted to the end cap 1014. In one embodiment, the rod 1016 is welded to the end cap 1014. The end cap 1014 and the rod 1016 can be made from any number of materials that are stiffer than a proximal end of a lead and are biocompatible. Suitable materials include metals, ceramics, plastics, and the like or combinations thereof. The end cap 1014 and the rod 1016 can be made from the same material or can be made from different materials.

Figure 10D:
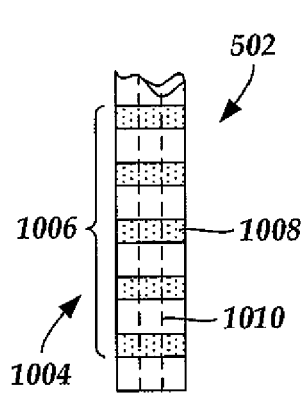
FIG. 10D is a schematic transverse cross-sectional view of one embodiment of a rod disposed in a central lumen of the proximal end of the lead shown in FIG. 11C, according to the invention.
Figure 10D:
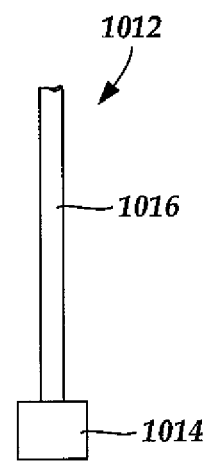
Figure 10D:
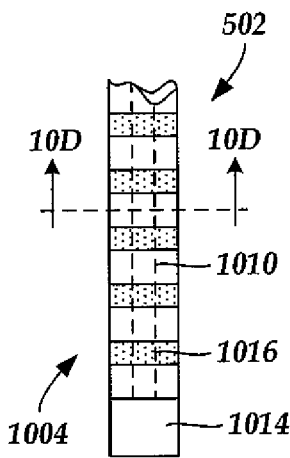
Figure 10D:
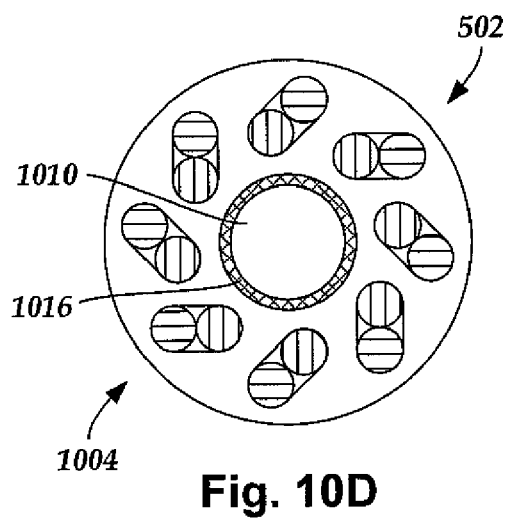

In at least some embodiments, the end plug 1012 is configured and arranged for disposal in the central lumen (1010 in FIG. 10A) of the proximal end (1004 in FIG. 10A) of the lead (502 in FIG. 10A). FIG. 10C is a schematic side view of one embodiment of the end cap 1014 and the rod 1016 disposed in the central lumen 1010 of the proximal end 1004 of the lead 502. FIG. 10D is a schematic transverse cross-sectional view of one embodiment of the rod 1016 disposed in the central lumen 1010 of the proximal end 1004 of the lead 502.

In at least some embodiments, when multiple conductive wires are disposed in an individual outer lumen of a lead, the multiple conductive wires can be electrically coupled to adjacent terminals disposed on a proximal end of the lead to facilitate assembly or repair of the lead. In at least some embodiments, when multiple conductive wires are disposed in an individual outer lumen of a lead, the multiple conductive wires can be electrically coupled to adjacent electrodes disposed on a distal end of the lead to facilitate assembly or repair of the lead. In at least some embodiments, when multiple conductive wires are disposed in an individual outer lumen of a lead, the multiple conductive wires can be electrically coupled to adjacent terminals disposed on a proximal end and adjacent electrodes disposed on the distal end of the lead to further facilitate assembly or repair of the lead.

Figures 11A, 11B, 11C:
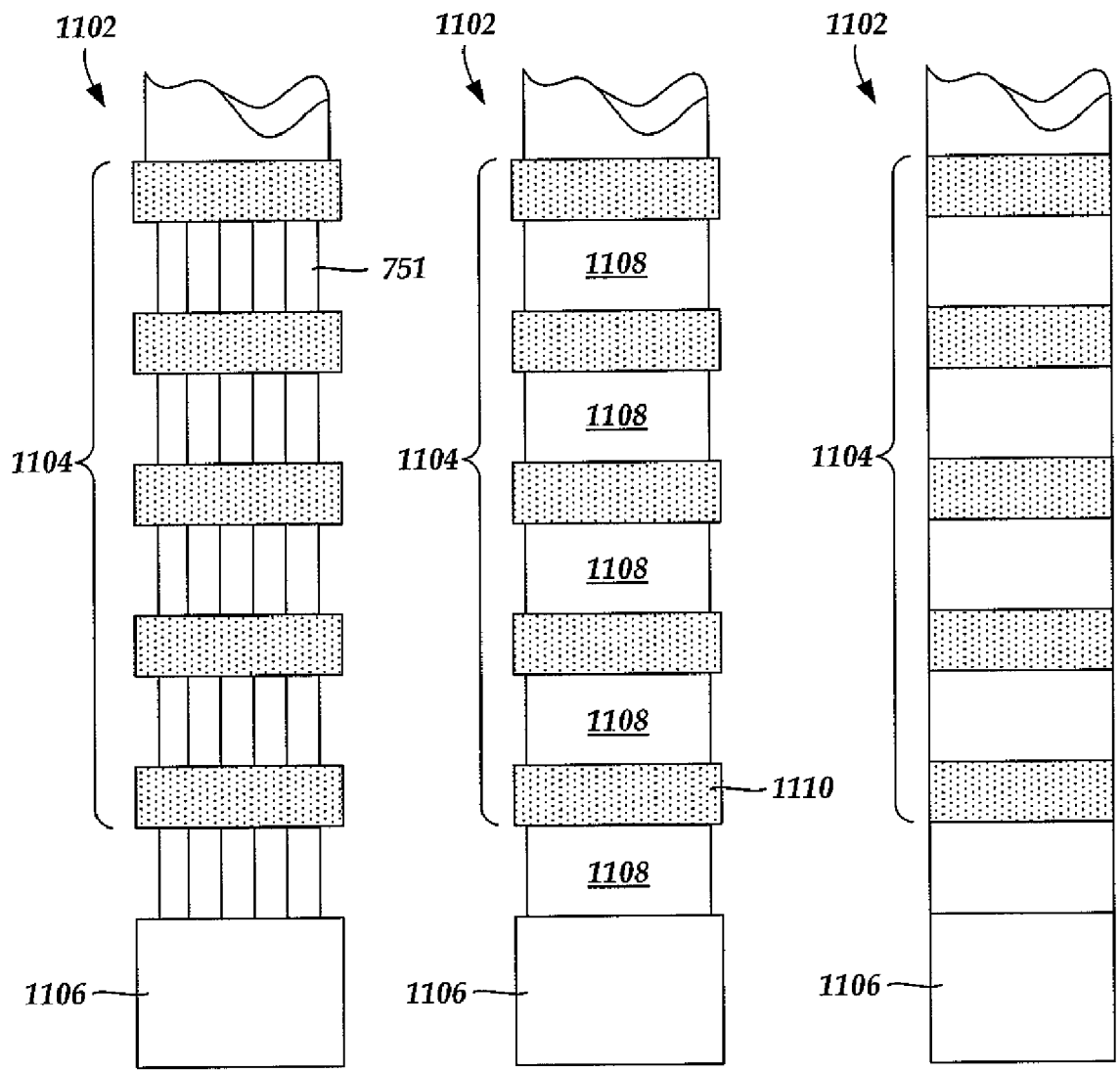
FIG. 11A is a schematic side view of one embodiment of a portion of a proximal end of a lead with oversized terminals and an oversized end cap and without spacers inserted between adjacent terminals and between the most proximal terminal and the end cap, according to the invention.
FIG. 11B is a schematic side view of one embodiment of the portion of the proximal end of the lead shown in FIG. 11A with resin injected between adjacent terminals and between the most proximal terminal and the end cap, according to the invention.
FIG. 11C is a schematic side view of one embodiment of the portion of the proximal end of the lead shown in FIG. 11B after the terminals and the end cap have been ground, according to the invention.

Sometimes spacers, such as polyurethane spacers, are formed and positioned between adjacent terminals on a proximal end of a lead. In at least some embodiments, in lieu of spacers, a resin can be injected between adjacent terminals and between the most proximal terminal and an end cap disposed on the proximal end of a lead. FIGS. 11A-11C show one embodiment of several possible steps performed during the fabrication of a proximal end of a lead. FIG. 11A is a schematic side view of one embodiment of a portion of a proximal end of a lead 1102 with terminals 1104 and an end cap 1106 disposed in a central lumen (744 in FIG. 7D). Conductive wires, such as conductive wires (912 and 914 in FIG. 9D), disposed in outer lumens, such as outer lumen 751, are electrically coupled to the terminals 1104.

FIG. 11B is a schematic side view of one embodiment of the portion of the proximal end of the lead 1102 with resin 1108 injected between adjacent terminals 1104 and between the most proximal terminal 1110 and the end cap 1106. Many different resins may be used. For example, the resin can be silicone, polyurethane, PEEK, epoxy, and the like or combinations thereof. For example, the resin can be liquid injected into a mold that contains the terminals and the end cap. In at least some embodiments, the resin can be injected by placing the proximal end of the lead 1102 into a mold cavity with cylindrical pockets sized to receive the terminals 1104 and the end cap 1106. The mold may be closed and the resin 1108 may be injected into the mold cavity to fill the spaces between the terminals 1304 and between the most proximal terminal 1110 and the end cap 1106. Additionally, in some embodiments, the resin 1108 may also fill any voids between the central lumen (744 in FIG. 7D) and the outer lumens (746-753 in FIG. 7D). In some embodiments, the resin 1108 may also fill any voids between an interior surface each outer lumen and an exterior surface of one or more connector wires disposed in each of the outer lumens.

Once the resin 1108 has been injected and set, the terminals 1104 may still have diameters that are greater than the diameters of the resin-filled spaces between adjacent terminals and between the most proximal terminal 1110 and the end cap 1106. In at least some embodiments, when the terminals 1104 and the end cap 1106 have a larger diameter than the resin-filled spaces, the terminals 1104 and the end cap 1106 can be ground down to a size and shape that is similar to the size and shape of the resin-filled spaces. FIG. 11C is a schematic side view of one embodiment of the portion of the proximal end of the lead 1102 after the terminals 1104 and the end cap 1106 have been ground. It will be understood that in some embodiments of the manufacturing process shown in FIGS. 11A-11C, the manufacturing process is performed without an end cap being disposed in the proximal end of the lead.

One advantage of using an injected resin to fill in spaces between adjacent terminals instead of using spacers is that a mold can be used to provide consistent spacing between adjacent terminals. Another advantage is that voids around conductive wires and lumens can be filled in to reduce relative movement between conductive wires and lumens. Yet another advantage is that resin can be used to facilitate attachment of the end cap to the proximal end of the lead. Another advantage is that using an injected resin may reduce assembly time during lead manufacture.

Figure 12:
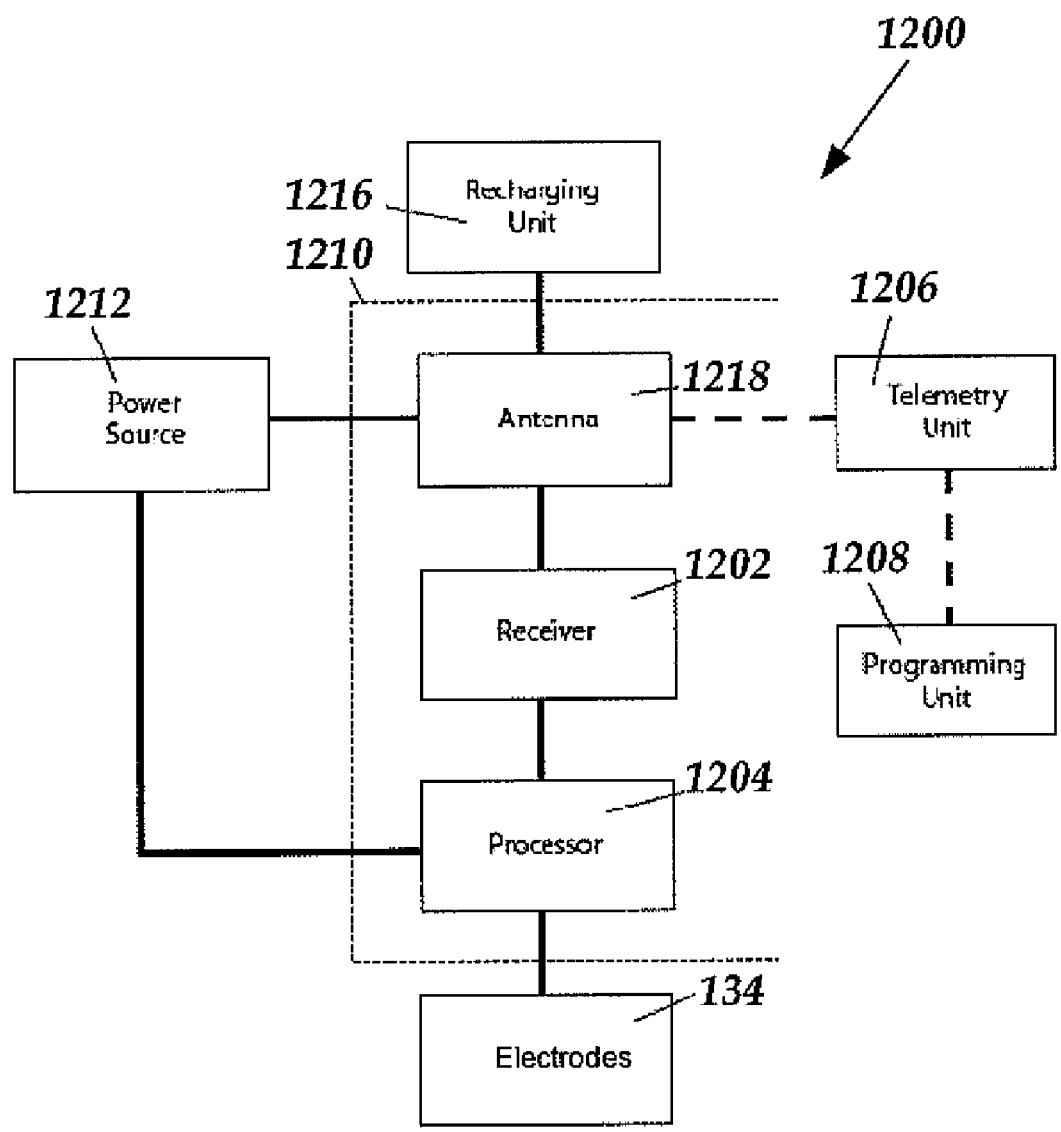
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead assembly comprising:
    a lead with a distal end, a proximal end, and a longitudinal length, the lead comprising
        a plurality of electrodes disposed at the distal end,
        a plurality of terminals disposed at the proximal end,
        at least one central lumen defined by the lead and extending along the longitudinal length of the lead from the proximal end to the distal end,
        a plurality of outer lumens defined by the lead and extending along the longitudinal length of the lead from the proximal end to the distal end, the plurality of outer lumens extending laterally from the at least one central lumen, wherein the plurality of outer lumens are each oval-shaped with a major axis, and
        a plurality of conductive wires extending along the longitudinal length of the lead, each conductive wire coupling at least one of the plurality of electrodes electrically to at least one of the plurality of terminals, wherein exactly two different conductive wires of the plurality of conductive wires are disposed in each of the plurality of outer lumens, the two different conductive wires each having an insulative coating to electrically insulate the two conductive wires from one another, and wherein each of the plurality of conductive wires has a diameter,
    wherein for each of the plurality of outer lumens the outer lumen has a width along the major axis that is equal to the sum of the diameters of the two conductive wires disposed in that outer lumen.

2. The lead assembly of claim 1, further comprising
    a lead splitter configured and arranged to electrically couple with the lead, the lead splitter having a distal end and a plurality of proximal tails, the lead splitter comprising
        a connector disposed at the distal end for receiving the proximal end of the lead, the connector comprising a connector housing defining at least one port for receiving the proximal end of the lead, and a plurality of connector contacts disposed in the connector housing, the connector contacts configured and arranged to couple electrically to at least one terminal on the proximal end of the lead, and
        each of the plurality of proximal tails having a distal end and comprising at least one lead-splitter terminal and at least one lead-splitter conductive wire, the lead-splitter terminal disposed at the distal end and the at least one lead-splitter conductive wire electrically coupling at least one of the plurality of connector contacts of the connector to the at least one lead-splitter terminal.

3. The lead assembly of claim 1, wherein for each of the plurality of outer lumens the major axis is disposed approximately perpendicular to a diameter of the lead which passes through a center of that outer lumen.

4. The lead assembly of claim 1, wherein for each of the plurality of outer lumens the major axis is disposed at an angle in the range of 15 to 60 degrees relative to a diameter of the lead which passes through a center of that outer lumen.

5. The lead assembly of claim 1, wherein the proximal end of the lead further comprises an end plug disposed in the at least one central lumen, the end plug configured and arranged to stiffen the proximal end of the lead to facilitate insertion of the proximal end of the lead into a connector.

6. The lead assembly of claim 1, wherein sixteen electrodes are disposed at the distal end of the lead.

7. The lead assembly of claim 1, wherein the entire longitudinal length of the lead is isodiametric.

8. The lead assembly of claim 1, wherein for each of the plurality of outer lumens the outer lumen is symmetrical about the major axis.

9. The lead assembly of claim 1, wherein the plurality of outer lumens extend the entire longitudinal length of the lead between the plurality of electrodes and the plurality of terminals.

10. The lead assembly of claim 1, wherein the plurality of conductive wires extend the entire longitudinal length of the lead between the plurality of electrodes and the plurality of terminals.

11. An electrical stimulating system comprising:
the lead assembly of claim 1;
a control module configured and arranged to electrically couple to the lead of the lead assembly, the control module comprising
a housing, and
an electronic subassembly disposed in the housing; and
a connector configured and arranged for receiving the lead of the lead assembly, the connector comprising
a connector housing defining at least one port for receiving the proximal end of the lead of the lead assembly, and
a plurality of connector contacts disposed in the connector housing, the connector contacts configured and arranged to couple to at least one terminal of the plurality of terminals disposed at the proximal end of the lead of the lead assembly.

12. The electrical stimulating system of claim 11, further including a lead splitter having a distal end and a plurality of proximal tails, the connector disposed on the distal end of the lead splitter.

13. The electrical stimulating system of claim 12, wherein each of the proximal tails of the lead splitter is configured and arranged for insertion into another connector.

14. A lead assembly comprising:
a lead with a distal end, a proximal end, and a longitudinal length, the lead comprising
a plurality of electrodes disposed at the distal end,
a plurality of terminals disposed at the proximal end,
at least one central lumen defined by the lead and extending along the longitudinal length of the lead from the proximal end to the distal end,
a plurality of outer lumens defined by the lead and extending along the longitudinal length of the lead from the proximal end to the distal end, the plurality of outer lumens extending laterally from the at least one central lumen, wherein the plurality of outer lumens are each oval-shaped with a major axis, and
a plurality of conductive wires extending along the longitudinal length of the lead, each conductive wire coupling at least one of the plurality of electrodes electrically to at least one of the plurality of terminals, wherein exactly two different conductive wires are disposed in each of the plurality of outer lumens, the two different conductive wires each having an insulative coating to electrically insulate the two conductive wires from one another, and wherein each of the plurality of conductive wires has a diameter,
wherein each of the plurality of outer lumens has an axis that is transverse to the major axis, and wherein for each of the plurality of outer lumens the outer lumen has a width along the transverse axis that is equal to the diameter of at least one of the two conductive wires disposed in that outer lumen.

15. The lead assembly of claim 14, wherein for each of the plurality of outer lumens the outer lumen is symmetrical about both the major axis and the transverse axis of that outer lumen.

16. The lead assembly of claim 14, further comprising
a lead splitter configured and arranged to electrically couple with the lead, the lead splitter having a distal end and a plurality of proximal tails, the lead splitter comprising
a connector disposed at the distal end for receiving the proximal end of the lead, the connector comprising a connector housing defining at least one port for receiving the proximal end of the lead, and a plurality of connector contacts disposed in the connector housing, the connector contacts configured and arranged to couple electrically to at least one terminal on the proximal end of the lead, and
each of the plurality of proximal tails having a distal end and comprising at least one lead-splitter terminal and at least one lead-splitter conductive wire, the lead-splitter terminal disposed at the distal end and the at least one lead-splitter conductive wire electrically coupling at least one of the plurality of connector contacts of the connector to the at least one lead-splitter terminal.

17. The lead assembly of claim 14, wherein for each of the plurality of outer lumens the major axis is disposed approximately perpendicular to a diameter of the lead which passes through a center of that outer lumen.

18. The lead assembly of claim 14, wherein for each of the plurality of outer lumens the major axis is disposed at an angle in the range of 15 to 60 degrees relative to a diameter of the lead which passes through a center of that outer lumen.

19. The lead assembly of claim 14, wherein sixteen electrodes are disposed at the distal end of the lead.

20. An electrical stimulating system comprising:
the lead assembly of claim 14;
a control module configured and arranged to electrically couple to the lead of the lead assembly, the control module comprising
a housing, and
an electronic subassembly disposed in the housing; and
a connector configured and arranged for receiving the lead of the lead assembly, the connector comprising
a connector housing defining at least one port for receiving the proximal end of the lead of the lead assembly, and
a plurality of connector contacts disposed in the connector housing, the connector contacts configured and arranged to couple to at least one terminal of the plurality of terminals disposed at the proximal end of the lead of the lead assembly.

* * * * *